(12) United States Patent
Hirakawa et al.

(10) Patent No.: US 9,791,356 B2
(45) Date of Patent: Oct. 17, 2017

(54) JOINT ANALYZING METHOD, PRODUCT DESIGNING METHOD, AND JOINT ANALYZING SYSTEM

(71) Applicant: SUBARU CORPORATION, Tokyo (JP)

(72) Inventors: Kazuaki Hirakawa, Tokyo (JP); Megumi Hiraki, Tokyo (JP); Kousaburou Akiba, Tokyo (JP)

(73) Assignee: SUBARU CORPORATION, Tokyo (JP)

( * ) Notice: Subject to any disclaimer, the term of this patent is extended or adjusted under 35 U.S.C. 154(b) by 63 days.

(21) Appl. No.: 14/971,654

(22) Filed: Dec. 16, 2015

(65) Prior Publication Data

US 2016/0178492 A1    Jun. 23, 2016

(30) Foreign Application Priority Data

Dec. 19, 2014   (JP) ................ 2014-257247

(51) Int. Cl.
  *G06F 17/50*    (2006.01)
  *G01N 3/02*     (2006.01)
  *G01N 3/00*     (2006.01)

(52) U.S. Cl.
  CPC ........... *G01N 3/02* (2013.01); *G01N 3/00* (2013.01); *G06F 17/5018* (2013.01); *G01N 2203/0216* (2013.01); *G01N 2203/0296* (2013.01)

(58) Field of Classification Search
  CPC .... G01N 3/02; G01N 3/00; G01N 2203/0296; G01N 2203/0216; G06F 17/5018
  (Continued)

(56) References Cited

U.S. PATENT DOCUMENTS 7,792,614 B2 *  9/2010  Giazotto ............... B60T 8/325
                                                   244/117 R

FOREIGN PATENT DOCUMENTS

JP    2001-134783 A    5/2001
JP    2004-322198 A    11/2004
(Continued)

OTHER PUBLICATIONS

Notification of Reasons for Refusal issued in corresponding Japanese Patent Application No. 2014-257247, dated Oct. 25, 2016.
(Continued)

*Primary Examiner* — Saif Alhija
(74) *Attorney, Agent, or Firm* — McDermott Will & Emery LLP (57) ABSTRACT

A joint analyzing method includes: performing a data measurement; performing a detailed analysis; performing a simplified analysis; performing a first repetition analysis in which the detailed analysis is repeated while modifying a first analysis model in which geometry of a joint surrounding region is modeled and an analysis technique in the detailed analysis, until a data measurement result and a detailed analysis result are brought into agreement; and performing a second repetition analysis in which the simplified analysis that takes into consideration an initial internal load of at least one junction in a load non-applied state obtained in the first repetition analysis is repeated while modifying a second analysis model rougher in element division of the geometry than the first analysis model and an analysis technique in the simplified analysis, until the data measurement result and a simplified analysis result are brought into agreement.

3 Claims, 5 Drawing Sheets (58) Field of Classification Search
USPC .............................................................. 703/1
See application file for complete search history.

(56) References Cited

FOREIGN PATENT DOCUMENTS

| | | |
|---|---|---|
| JP | 2004-347571 A | 12/2004 |
| JP | 2007-114061 A | 5/2007 |
| JP | 2014-063262 A | 4/2014 |

OTHER PUBLICATIONS

Decision to Grant issued in corresponding Japanese Patent Application No. 2014-257247, dated Jan. 4, 2017.

* cited by examiner

JOINT ANALYZING METHOD, PRODUCT DESIGNING METHOD, AND JOINT ANALYZING SYSTEM

CROSS-REFERENCE TO RELATED APPLICATIONS

The present application claims priority from Japanese Patent Application No. 2014-257247 filed on Dec. 19, 2014, the entire contents of which are hereby incorporated by reference.

BACKGROUND

The technology relates to a joint analyzing method and a joint analyzing system for performing a structural analysis of a joint that joins two or more members together, and to a product designing method for designing a product having the joint.

A structural analysis by means of a finite element method (FEM) has been widely used in designing of a joint that joins two or more members together. For example, reference is made to Japanese Unexamined Patent Application Publication No. 2004-322198.

The joint contains a large number of elements that are difficult to be modeled, examples of which may include an initial joining load and a state of contact between a joining material and a base material. In general, to address such a difficulty in modeling of the joint, an analysis model may be divided into fine meshes to achieve a high degree of accuracy, or an analysis result may be multiplied by a large safety factor to make the base member large in thickness.

SUMMARY

Dividing an analysis model into excessively fine meshes leads obviously to a large data amount, which in turn results in difficulty in completing an analysis, a heavy analysis process, or any other concern. Hence, this approach may allow for processing of the analysis that is directed only to a region around the joint, but may raise a concern, for example, that an analysis result may not be obtained or a process may be difficult to be performed, upon the analysis of a large product having multiple joints.

Also, multiplying an analysis result by a large safety factor to make a base member large in thickness not only leads obviously to an increase in weight but it also means nothing more or less than that the analysis of the joint has not been performed at a high degree of accuracy in the first place, meaning that there is room for improvement in such an analysis method of the joint itself.

It is desirable to perform a structural analysis of a joint at a high degree of accuracy by an analysis model that is small in data amount.

A first aspect of the technology provides a joint analyzing method that includes: performing a data measurement in which measurement of data on one or more of stress, strain, and deformation of a joint in each of a load non-applied state and a load applied state is performed, in which the joint joins two or more members together by at least one junction, the load non-applied state is a state in which an external load is unapplied to the joint, and the load applied state is a state in which the external load is applied to the joint; performing a detailed analysis in which a finite element method analysis is performed using a first analysis model in which geometry of a joint surrounding region is modeled; performing a simplified analysis in which a finite element method analysis is performed using a second analysis model in which the at least one junction is eliminated or simplified and geometry of the joint surrounding region is rougher in element division than the geometry in the first analysis model in the detailed analysis; performing a first repetition analysis in which the detailed analysis is repeated while modifying the first analysis model and an analysis technique of the finite element method in the detailed analysis, until a measurement result of the data measurement and an analysis result of the detailed analysis are brought into agreement with each other within a first predetermined error range, in which the first repetition analysis obtains an initial internal load of the at least one junction in the load non-applied state and allows the simplified analysis to take into consideration the initial internal load; and performing a second repetition analysis in which the simplified analysis that takes into consideration the initial internal load is repeated while modifying the second analysis model and an analysis technique of the finite element method in the simplified analysis, until the measurement result of the data measurement and an analysis result of the simplified analysis are brought into agreement with each other within a second predetermined error range.

In a preferred aspect, the data measurement and the detailed analysis each may obtain strain and deformation of each of the two or more members in the load applied state and geometry of a joining member in the load non-applied state, and the simplified analysis may obtain strain and deformation of each of the two or more members in the load applied state.

A second aspect of the technology provides a product designing method that includes: using the second analysis model of the joint and the analysis technique of the finite element method in the simplified analysis which are obtained upon establishment of the second repetition analysis in the joint analyzing method according to the first aspect or the preferred aspect; and performing designing and analysis of a product having the joint.

A third aspect of the technology provides a joint analyzing system that includes: a data measurement unit that performs measurement of data on one or more of stress, strain, and deformation of a joint in each of a load non-applied state and a load applied state, in which the joint joins two or more members together by at least one junction, the load non-applied state is a state in which an external load is unapplied to the joint, and the load applied state is a state in which the external load is applied to the joint; and an analyzer that performs: a detailed analysis in which a finite element method analysis is performed by a first analysis model in which geometry of a joint surrounding region is modeled; a simplified analysis in which a finite element method analysis is performed by a second analysis model in which the at least one junction is eliminated or simplified and geometry of the joint surrounding region is rougher in element division than the geometry in the first analysis model in the detailed analysis; a first repetition analysis in which the detailed analysis is repeated while modifying the first analysis model and an analysis technique of the finite element method in the detailed analysis, until a measurement result of the data measurement and an analysis result of the detailed analysis are brought into agreement with each other within a first predetermined error range, in which the first repetition analysis obtains an initial internal load of the at least one junction in the load non-applied state and allows the simplified analysis to take into consideration the initial internal load; and a second repetition analysis in which the simplified analysis that takes into consideration the initial internal load is repeated while modifying the second analysis model and an analysis technique of the finite element method in the simplified analysis, until the measurement result of the data measurement and an analysis result of the simplified analysis are brought into agreement with each other within a second predetermined error range.

DETAILED DESCRIPTION

In the following, some implementations of the technology are described in detail with reference to the accompanying drawings.

[Configuration of Joint Analyzing System]

First, a description is given of a configuration of a joint analyzing system 10 according to one implementation.

Figure 1:
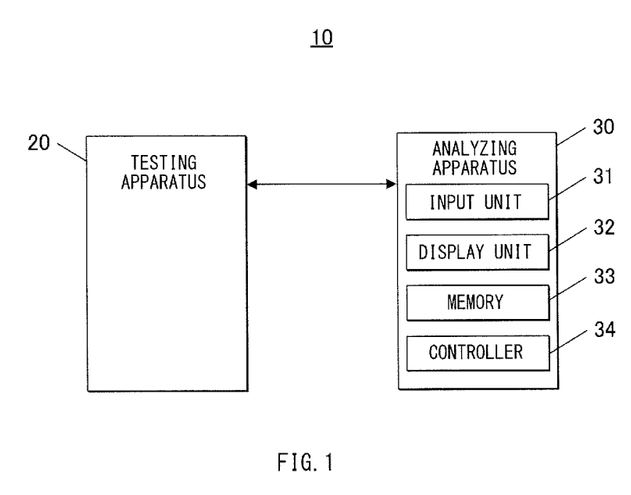
FIG. 1 is a block diagram illustrating an outline configuration of a joint analyzing system.

FIG. 1 is a block diagram illustrating an outline configuration of the joint analyzing system 10.

The joint analyzing system 10 involves establishing, through an actual measurement test and a structural analysis, favorable analysis conditions on a joint by which two or more members are joined together, and may further involve utilizing the thus-established analysis conditions on the joint to perform designing of a product having that joint.

Referring to FIG. 1, the joint analyzing system 10 may include a testing apparatus 20 and an analyzing apparatus 30.

The testing apparatus 20 may be operable to perform various tests including a tensile test without limitation. More specifically, the testing apparatus 20 may be operable to perform a data measurement test to be described later.

The analyzing apparatus 30 may be operable to perform a detailed joint analysis and a simplified joint analysis to be described later. The analyzing apparatus 30 may include, for example but not limited to, an input unit 31, a display unit 32, a memory 33, and a controller 34. The input unit 31 may receive a user operation. The display unit 32 may include an unillustrated display. The memory 33 may store any software such as, but not limited to, computer-aided design (CAD) software and analysis software. The controller 34 may perform an integrated control of each part of the joint analyzing system 10.

[Product Designing Method]

A description is given next of a product designing method for designing a product having the joint using the joint analyzing system 10.

Figure 2:
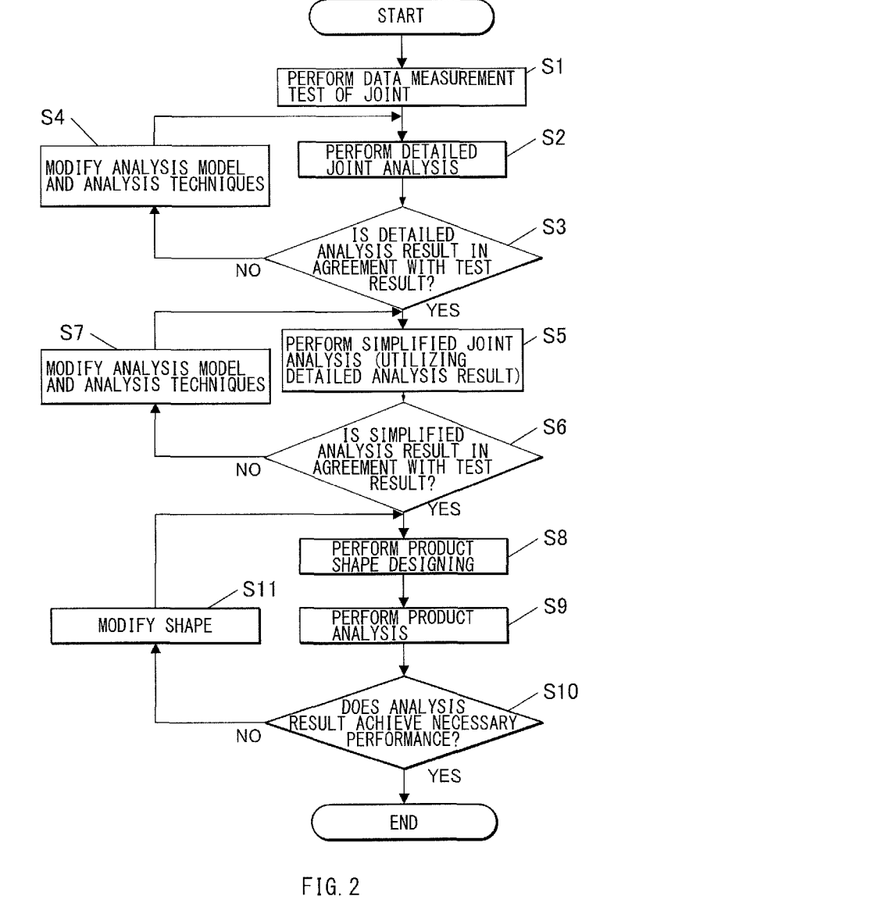
FIG. 2 is a flowchart illustrating a flow of a product designing method.
Figure 3A:
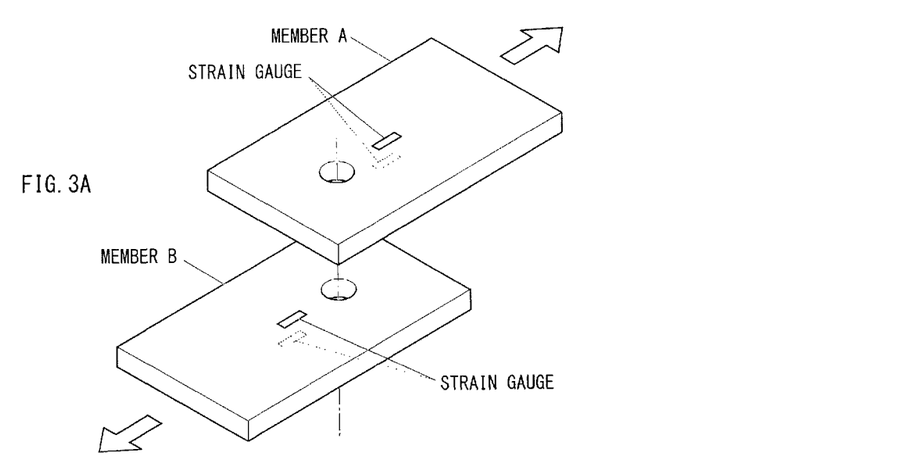
FIGS. 3A and 3B illustrate examples of test specimens in a data measurement test.
Figure 3B:
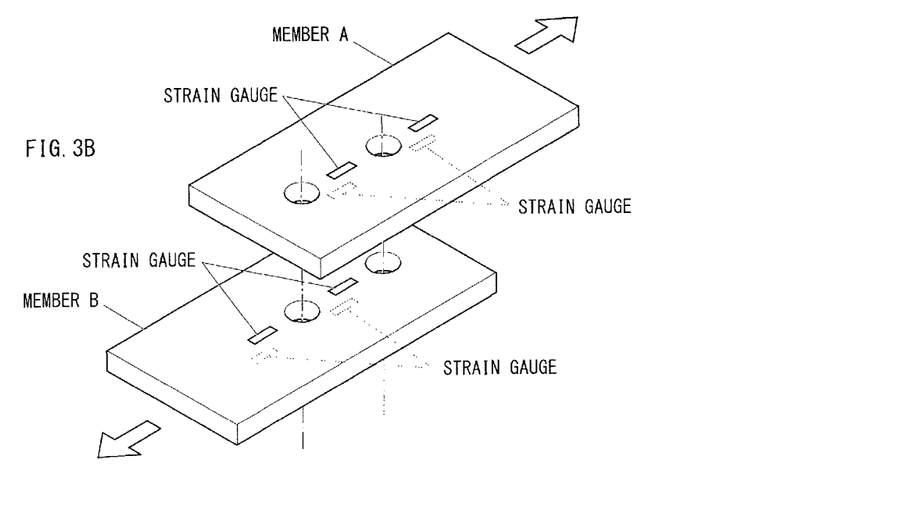
Figure 4:
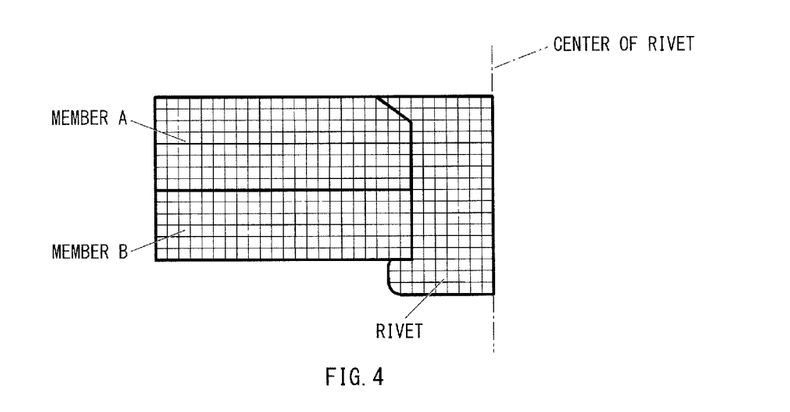
FIG. 4 illustrates an example of an analysis model in a detailed joint analysis.
Figure 5:
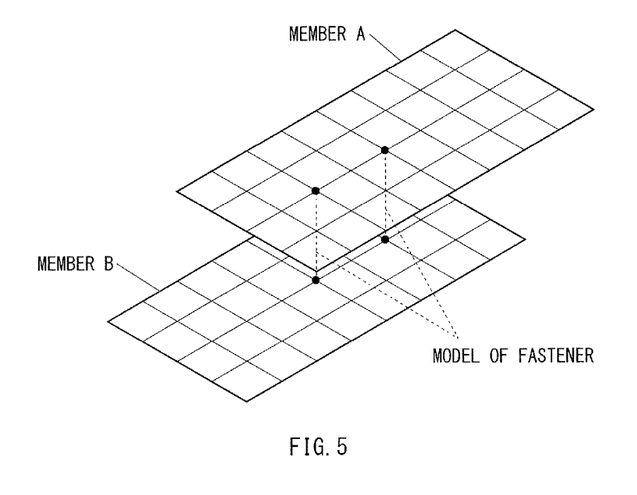
FIG. 5 illustrates an example of an analysis model in a simplified joint analysis.
Figure 6:
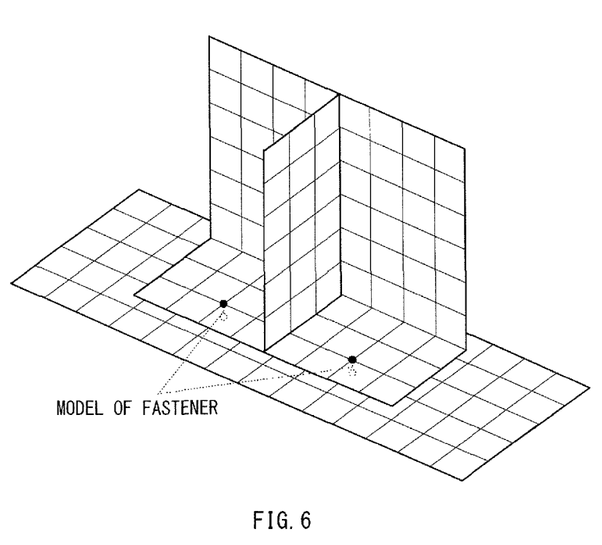
FIG. 6 illustrates an example of an analysis model in a product analysis.

FIG. 2 is a flowchart illustrating a flow of the product designing method. FIGS. 3A and 3B illustrate examples of test specimens in the data measurement test to be described later. FIGS. 4 to 6 illustrate examples of respective analysis models in the detailed joint analysis, the simplified joint analysis, and a product analysis which are to be described later.

The product designing method according to one implementation involves establishing an analysis model of a joint that joins two members together first, and designing and analysis of a product having that joint thereafter. A material on which the designing and the analysis are performable by the product designing method is not particularly limited. Non-limiting examples of such a material may include a metal material, a composite material such as fiber-reinforced plastics (FRP), and a sintered material such as ceramics.

As used herein, the term "joint" refers to a structural part in which two members are joined together by one or more junctions. For example, the "joint" may refer to: a fastened part by means of a fastener such as, but not limited to, a bolt and a rivet; a weld part using a weld member; an adhesion part using an adhesion member; or any other structural part in which two members are joined together by one or more junctions. The term "joint surrounding region" refers to a part of the joined two members which is around the joint including the joint itself and which includes a region in which strength derived from a structure of the joint is influential.

More specifically, a joint analyzing method according to one implementation first carries out the data measurement test that performs an actual measurement of data on stress, strain, and deformation of the joint (step S1), as illustrated in FIG. 2.

Referring to FIGS. 3A and 3B, external loads may be applied to respective two joined members A and B in opposite directions from each other in the data measurement test. The external loads each may be, for example but not limited to, a tensile load or a compressive load. Then, one or both of the strain and thermal strain of each of the members A and B may be measured by strain gauges attached to both sides of each of the members A and B at positions in the load-applying directions relative to the junctions of the respective members A and B, and an unillustrated displacement gauge may be used to measure deformation of each of the members A and B. The stress may be calculated from the strain. Also, geometry of a joining member and the strain of each of the members A and B may be measured in a state in which the two members A and B are joined only and no external loads are applied thereto (hereinafter referred to as a "load non-applied state"). The joining member may be, for example but not limited to, the fastener, the adhesion member, or the weld member. FIGS. 3A and 3B illustrate examples of test specimens in which the two members A and B are joined together by the unillustrated fastener inserted into holes. FIG. 3A illustrates an example in which one junction is provided, whereas FIG. 3B illustrates an example in which two junctions are provided.

The following Table 1 illustrates a specific but non-limiting content of each test performed in the data measurement test.

In Table 1, the "Area of Junction" refers to area such as, but not limited to, cross-sectional area of the fastener, adhesion area, and weld area. The "Thermal Load" for the item "Kind of External Load" and "Thermal Strain" for the item "Obtained Data" are both taken into consideration only in a case that involves generation of a thermal load, e.g., when the joint is exposed under a thermal environment, when the joining is based on welding, or any other case that involves heat.

TABLE 1

| Item | | Content |
|---|---|---|
| Kind of External Load | | Fastening Load, Tensile Load, Compressive Load, and Thermal Load |
| Kind of Structure | Number of Junctions | One Junction, or Two or More Junctions |
| | Thickness of Members | 5:5, 7:3, or 3:7 |
| | Area of Junction | Small, Medium, or Large |
| Obtained Data | | Geometry of Joining Member and Strain of Each Member in Load Non-applied state Strain, Deformation, and Thermal Strain of Each Member in Load Applied State |

Next, the detailed joint analysis that analyzes the joint surrounding region in detail is performed (step S2). The detailed joint analysis is performed for a purpose of obtaining an initial internal load generated at the junction in the load non-applied state. The initial internal load may be, for example but not limited to, initial fastening force derived from the fastener, an internal load resulting from pressure insertion, pressure bonding force, or the thermal load.

More specifically, the detailed joint analysis uses an analysis model in which geometry of the joint surrounding region is accurately reflected and divided into fine meshes (elements) as illustrated in FIG. 4 to perform a structural analysis by means of a finite element method (FEM). FIG. 4 illustrates an example of the analysis model in which the two members A and B are joined together by a rivet. The analysis model illustrated in FIG. 4 may be an axisymmetric model that uses a plane element.

The following Table 2 illustrates examples of data obtained from the detailed joint analysis and analysis techniques of the finite element method in the detailed joint analysis.

Referring to Table 2, the geometry of the joining member and the strain of each of the members A and B in the load non-applied state as well as the strain and the deformation of each of the members A and B in a load applied state may be obtained from the detailed joint analysis. As described later in detail, the thus-obtained pieces of data are obtained as parameters for bringing an analysis result of the detailed joint analysis in correspondence with a result obtained from the data measurement test, and the initial internal load generated at the junction in the load non-applied state is obtained ultimately from the detailed joint analysis.

TABLE 2

| Type of Analysis | Obtained Data | Analysis Technique | |
|---|---|---|---|
| Detailed Joint Analysis | Geometry of Joining Member and Strain of Each Member in Load Non-Applied State | Dynamic Analysis | Geometric Non-Linear Analysis and Material Non-Linear Analysis |
| | Strain and Deformation of Each Member in Load Applied State | Static Analysis | Structural Analysis and Thermal Stress Analysis |
| | | Dynamic Analysis | Geometric Non-Linear Analysis and Material Non-Linear Analysis |

Next, a determination is made as to whether the measurement result obtained from the data measurement test in the step S1 and the analysis result obtained from the detailed joint analysis in the step S2 are in favorable agreement with each other (step S3).

More specifically, in the step S3, the geometry of the joining member and the strain of each of the members A and B in the load non-applied state as well as the strain and the deformation of each of the members A and B in the load applied state, which are obtained from both the data measurement test and the detailed joint analysis, may be individually compared between the data measurement test and the detailed joint analysis to determine whether the parameters to be compared fall within their predetermined error ranges. The compared parameters may be determined as being in favorable agreement with each other between the measurement result of the data measurement test and the analysis result of the detailed joint analysis, when the compared parameters therebetween are determined as falling within their respective predetermined error ranges. Note that the error ranges upon the comparison may be set individually for the compared parameters.

When the measurement result of the data measurement test and the analysis result of the detailed joint analysis are determined as not being in favorable agreement with each other in the step S3 (No in the step S3), i.e., when any one of the parameters is determined as not being in agreement between the data measurement test and the detailed joint analysis, the analysis model and analysis techniques in the detailed joint analysis may be modified (step S4), following which the process may move back to the foregoing step S2 where the detailed joint analysis is performed again using the modified analysis model and the modified analysis techniques to perform the comparison and the determination in the step S3 again. As used herein, the term "analysis model" refers to element geometry and an element type, as well as various physical properties such as, but not limited to, a friction coefficient. The term "analysis techniques" refer to a static analysis and a dynamic analysis. The static analysis may include utilization of a factor such as, but not limited to, thermal stress. The dynamic analysis may include a solution such as, but not limited to, an explicit method and an implicit method.

In the foregoing case, the detailed joint analysis is repeated while the analysis model and the analysis techniques are modified, until the measurement result of the data measurement test and the analysis result of the detailed joint analysis are brought into agreement with each other within the predetermined error ranges. This makes it possible to obtain, with a high degree of accuracy, the initial internal load generated at the junction in the load non-applied state from the analysis result of the detailed joint analysis which has been brought in correspondence with the measurement result of the data measurement test, despite the fact that the actual measurement of such an initial internal load is difficult by the data measurement test. Note that the modification of the analysis model and the analysis techniques in the detailed joint analysis in the step S4 may be so performed on an as-needed basis that the errors in the respective compared parameters become small, based on a result of the comparison performed in the step S3.

When the measurement result of the data measurement test and the analysis result of the detailed joint analysis are determined as being in favorable agreement with each other in the step S3 (Yes in the step S3), the simplified joint analysis is performed that analyzes the joint surrounding region in a more simplified fashion than the detailed joint analysis (step S5). The simplified joint analysis may be performed for a purpose of establishing an analysis model of the joint which is small in data amount.

More specifically, the simplified joint analysis uses an analysis model in which the junction is eliminated or simplified and geometry of the joint surrounding region is divided into meshes rougher than the geometry in the analysis model of the detailed joint analysis as illustrated in FIG. 5 to perform the structural analysis by means of the finite element method. A mesh size of each mesh in the analysis model of the simplified joint analysis may be half the size of each fastener or less.

In the simplified joint analysis, instead of modeling the junction accurately, the initial internal load generated at the junction in the load non-applied state may be set to corresponding nodes in each of the members A and B, based on the analysis result of the detailed joint analysis in which the agreement with the measurement result of the data measurement test has been confirmed. FIG. 5 illustrates an example of the analysis model in which the two members A and B are joined together by two fasteners. The analysis model illustrated in FIG. 5 may be a surface model where the members A and B are each modeled in a plane element.

The following Table 3 illustrates examples of data obtained from the simplified joint analysis and analysis techniques of the finite element method in the simplified joint analysis.

Referring to Table 3, the strain and the deformation of each of the members A and B in the load applied state may be obtained from the simplified joint analysis.

TABLE 3

| Type of Analysis | Obtained Data | Analysis Technique | |
|---|---|---|---|
| Simplified Joint Analysis | Strain and Deformation of Each Member in Load Applied State | Static Analysis Dynamic Analysis | Structural Analysis and Thermal Stress Analysis Geometric Non-Linear Analysis and Material Non-Linear Analysis |

Next, a determination is made as to whether the measurement result obtained from the data measurement test in the step S1 and an analysis result obtained from the simplified joint analysis in the step S5 are in favorable agreement with each other (step S6).

More specifically, in the step S6, the strain and the deformation of each of the members A and B in the load applied state, which are obtained from both the data measurement test and the simplified joint analysis, may be individually compared between the data measurement test and the simplified joint analysis to determine whether parameters to be compared fall within their predetermined error ranges. The compared parameters may be determined as being in favorable agreement with each other between the measurement result of the data measurement test and the analysis result of the simplified joint analysis, when the compared parameters therebetween are determined as falling within their respective predetermined error ranges. Note that the error ranges upon the comparison may be set individually for the compared parameters.

When the measurement result of the data measurement test and the analysis result of the simplified joint analysis are determined as not being in favorable agreement with each other in the step S6 (No in the step S6), i.e., when any one of the parameters is determined as not being in agreement between the data measurement test and the simplified joint analysis, the analysis model and analysis techniques in the simplified joint analysis may be modified (step S7), following which the process may move back to the foregoing step S5 where the simplified joint analysis is performed again using the modified analysis model and the modified analysis techniques to perform the comparison and the determination in the step S6 again.

In the foregoing case, the simplified joint analysis that takes into consideration the initial internal load of the junction obtained from the repetition process ranging from the steps S2 to S4 is repeated while the analysis model and the analysis techniques in the simplified joint analysis are modified, until the measurement result of the data measurement test and the analysis result of the simplified joint analysis are brought into agreement with each other within the predetermined error ranges. This makes it possible to obtain the analysis conditions on the joint, i.e., conditions including the analysis model and the analysis techniques, which are high in analysis accuracy and small in data amount. Note that the modification of the analysis model and the analysis techniques in the simplified joint analysis in the step S7 may be so performed on an as-needed basis that the errors in the respective compared parameters become small, based on a result of the comparison performed in the step S6.

When the measurement result of the data measurement test and the analysis result of the simplified joint analysis are determined as being in favorable agreement with each other in the step S6 (Yes in the step S6), the analysis conditions derived from the simplified joint analysis performed at this time fulfill the establishment of the analysis conditions on the joint which are high in analysis accuracy and small in data amount.

Next, the process may move on to product designing that uses the thus-obtained analysis conditions on the joint. First, detailed designing on a shape of the product having the joint is performed (step S8).

Next, the product designed in the step S8 may be analyzed (step S9).

In the step S9, as illustrated by way of example in FIG. 6, the analysis conditions of the simplified joint analysis in which the agreement with the measurement result of the data measurement test has been confirmed in the step S6 may be used for the analysis of each joint in the product.

The following Table 4 illustrates examples of data obtained from the product analysis and analysis techniques of the finite element method in the product analysis.

Referring to Table 4, the strain and the deformation of each of the members in the load applied state may be obtained from the product analysis.

TABLE 4

| Type of Analysis | Obtained Data | Analysis Technique | |
|---|---|---|---|
| Product Analysis | Strain and Deformation of Each Member in Load Applied State | Static Analysis Dynamic Analysis | Structural Analysis and Thermal Stress Analysis Geometric Non-Linear Analysis and Material Non-Linear Analysis |

Next, a determination may be made as to whether a result of the product analysis performed in the step S9 satisfies predetermined necessary performance (step S10). The shape may be modified (step S11) when the result of the product analysis is determined as not satisfying the predetermined necessary performance (No in the step S10), following which the process may move back to the foregoing step S8 to perform respectively the product shape designing and the product analysis in the steps S8 and S9 again on the basis of the modified shape, and to perform the determination in the step S10 again.

The product designing may be completed when the result of the product analysis is determined as satisfying the predetermined necessary performance in the step S10 (Yes in the step S10).

EXAMPLE EFFECTS

In the foregoing implementation, the analysis result of the detailed joint analysis is first brought into agreement with the measurement result of the data measurement test to calculate the initial internal load with a high degree of accuracy. Here, the detailed joint analysis is based on the analysis model that is accurate in geometry of the joint surrounding region. The data measurement test is based on the actual measurement of the data on stress, strain, and deformation of the joint. The initial internal load is generated at the junction in the load non-applied state and is difficult to be measured by the actual measurement.

Then, the analysis result of the simplified joint analysis that takes into consideration the thus-calculated initial internal load of the junction is brought into agreement with the measurement result of the data measurement test. Here, the simplified joint analysis is based on the analysis model in which the junction is eliminated or simplified and which is rougher in the element division than the analysis model of the detailed joint analysis. Thus, using the analysis conditions, i.e., the conditions including the analysis model and the analysis techniques, used in the simplified joint analysis whose analysis result has been brought into agreement with the measurement result of the data measurement test make it possible to establish the analysis conditions on the joint which are high in analysis accuracy and small in data amount.

Hence, it is possible to perform the structural analysis of the joint at a high degree of accuracy by the analysis model that is small in data amount, as compared with an example where an analysis model is simply divided into fine meshes.

Also, the thus-established analysis conditions of the joint may be used to perform the designing and the analysis of the overall product having the joint. Hence, it is possible to calculate strength of the overall product more accurately, which in turn makes it possible to achieve a reduction in weight while satisfying necessary strength without wastefully providing excess thickness.

Although some preferred implementations of the technology have been described in the foregoing by way of example with reference to the accompanying drawings, the technology is by no means limited to the implementations described above. It should be appreciated that modifications and alterations may be made by persons skilled in the art without departing from the scope as defined by the appended claims. The technology is intended to include such modifications and alterations in so far as they fall within the scope of the appended claims or the equivalents thereof.

For example, although the description has been given of the foregoing implementation with reference to an example of the joint to which two members are joined, the analysis is likewise performable to a joint to which two or more members are joined.

Also, although the data measurement test performs the actual measurement of the data on stress, strain, and deformation, the data on one or more of the stress, the strain, and the deformation may be subjected to the actual measurement. Such data on one or more of the stress, the strain, and the deformation having been subjected to the actual measurement may be used for the comparison performed with respect to the analysis results described above.

The invention claimed is:

1. A product designing method, comprising:
   performing, by a testing apparatus, a data measurement in which measurement of data on one or more of stress, strain, and deformation of a joint in each of a load non-applied state and a load applied state is performed, the joint joining two or more members together by at least one junction, the load non-applied state being a state in which an external load is unapplied to the joint, and the load applied state being a state in which the external load is applied to the joint;
   performing, by an analyzer, a first analysis in which a finite element method analysis is performed using a first analysis model in which geometry of a joint surrounding region is modeled;
   performing, by the analyzer, a second analysis in which a finite element method analysis is performed using a second analysis model in which the at least one junction is eliminated or simplified and geometry of the joint surrounding region is meshed rougher in element division than the geometry meshed in the first analysis model in the first analysis;
   performing, by the analyzer, a first repetition analysis in which the first analysis is repeated while modifying the first analysis model and an analysis technique of the finite element method in the first analysis, until a measurement result of the data measurement and an analysis result of the first analysis are brought into agreement with each other within a first predetermined error range, the first repetition analysis obtaining an initial internal load of the at least one junction in the load non-applied state and allowing the second analysis to take into consideration the initial internal load;
   performing, by the analyzer, a second repetition analysis in which the second analysis that takes into consideration the initial internal load is repeated while modifying the second analysis model and an analysis technique of the finite element method in the second analysis, until the measurement result of the data measurement and an analysis result of the second analysis are brought into agreement with each other within a second predetermined error range;
   using, by the analyzer, the second analysis model of the joint and the analysis technique of the finite element method in the second analysis which are obtained upon establishment of the second repetition analysis; and
   performing, by the analyzer, designing and analysis of a product having the joint.

2. The product designing method according to claim 1, wherein
   the data measurement and the first analysis each obtain strain and deformation of each of the two or more members in the load applied state and geometry of a joining member in the load non-applied state, and
   the second analysis obtains strain and deformation of each of the two or more members in the load applied state.

3. A joint analyzing system, comprising:
   a data measurement unit that performs measurement of data on one or more of stress, strain, and deformation of a joint in each of a load non-applied state and a load applied state, the joint joining two or more members together by at least one junction, the load non-applied state being a state in which an external load is unapplied to the joint, and the load applied state being a state in which the external load is applied to the joint; and
   an analyzer that performs:

a first analysis in which a finite element method analysis is performed by a first analysis model in which geometry of a joint surrounding region is modeled;

a second analysis in which a finite element method analysis is performed by a second analysis model in which the at least one junction is eliminated or simplified and geometry of the joint surrounding region is meshed rougher in element division than the geometry in the first analysis model in the first analysis;

a first repetition analysis in which the first analysis is repeated while modifying the first analysis model and an analysis technique of the finite element method in the first analysis, until a measurement result of the data measurement and an analysis result of the first analysis are brought into agreement with each other within a first predetermined error range, the first repetition analysis obtaining an initial internal load of the at least one junction in the load non-applied state and allowing the second analysis to take into consideration the initial internal load;

a second repetition analysis in which the second analysis that takes into consideration the initial internal load is repeated while modifying the second analysis model and an analysis technique of the finite element method in the second analysis, until the measurement result of the data measurement and an analysis result of the second analysis are brought into agreement with each other within a second predetermined error range; and designing and analyzing a product having the joint by using the second analysis model of the joint and the analysis technique of the finite element method in the second analysis which are obtained upon establishment of the second repetition analysis.

* * * * *